United States Patent [19]

Durr et al.

[11] 4,051,258

[45] Sept. 27, 1977

[54] THIOUREA DERIVATIVES FOR COMBATTING MITES AND TICKS

[75] Inventors: Dieter Durr, Bottmingen; Marcus von Orelli, Munchenstein, both of Switzerland

[73] Assignee: Ciba-Geigy Corporation, Ardsley, N.Y.

[21] Appl. No.: 623,875

[22] Filed: Oct. 20, 1975

Related U.S. Application Data

[62] Division of Ser. No. 379,536, July 6, 1973, Pat. No. 3,927,087.

[30] Foreign Application Priority Data

July 24, 1972    Switzerland .................. 11003/72

[51] Int. Cl.$^2$ .......................... A01N 9/12
[52] U.S. Cl. ..................... 424/322; 424/285; 424/302
[58] Field of Search ............. 424/322; 260/552 R

[56] References Cited

U.S. PATENT DOCUMENTS

| 2,651,620 | 12/1950 | Hill et al. ............... 260/553 A |
| 2,723,192 | 11/1955 | Todd ...................... 260/553 A |
| 3,365,360 | 1/1968 | Taylor ..................... 424/322 |
| 3,395,233 | 7/1968 | Duerr et al. ............. 260/552 R |
| 3,801,635 | 4/1974 | Duerr et al. ............. 260/552 R |
| 3,927,087 | 12/1975 | Duerr et al. ............. 260/552 R |

FOREIGN PATENT DOCUMENTS 1,555,793    1/1969    France

*Primary Examiner*—Leonard Schenkman
*Attorney, Agent, or Firm*—Frederick H. Rabin

[57] ABSTRACT

New thioureas corresponding to the formula

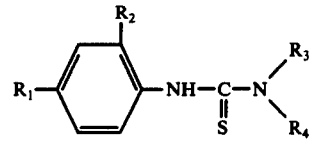

wherein
  $R_1$ represents halogen or the methyl group,
  $R_2$ represents $C_1$-$C_4$ alkyl,
  $R_3$ represents methyl or allyl and
  $R_4$ represents $C_2$-$C_5$ alkyl, $C_3$-$C_5$ alkenyl, $C_3$-$C_5$ alkynyl or hydroxy- or cyano-substituted alkyl, benzyl, cycloalkyl-alkyl, or tetrahydrofurylalkyl, which are useful for the control of arachnida, particularly ticks.

11 Claims, No Drawings

THIOUREA DERIVATIVES FOR COMBATTING MITES AND TICKS

This is a division of application Ser. No. 379,536, filed on July 6, 1973, now U.S. Pat. No. 3,927,087.

The present invention relates to new thioureas, to processes for their production, as well as to agents and methods for the control of arachnida by application of the new thioureas as active substances.

The new thioureas correspond to formula I

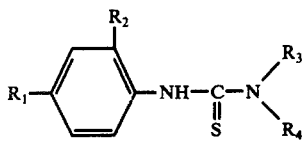

wherein
- $R_1$ represents halogen, preferably chlorine or bromine, or the methyl group
- $R_2$ represents $C_1$–$C_4$-alkyl, preferably $C_1$–$C_2$-alkyl,
- $R_3$ represents methyl or allyl,
- $R_4$ represents $C_2$–$C_5$-alkyl, $C_3$–$C_5$-alkenyl, $C_3$–$C_5$-alkynyl, or hydroxy- or cyano-substituted alkyl, benzyl, cycloalkyl-alkyl or tetrahydrofurylalkyl.

Alkyl radicals are the methyl, ethyl, n-propyl, isopropyl n-butyl, isobutyl, sec-butyl or tert.-butyl radicals; and in the case of $R_4$ also the n-pentyl radical and its isomers. These radicals can be substituted by halogen — by which is meant fluorine, chlorine, bromine or iodine, preferably fluorine, chlorine or bromine — hydroxy or cyano. By alkenyl or alkynyl radicals are meant preferably propenyl, butenyl or propynyl or butynyl radicals, which can be mono- or polysubstituted or methyl. To be mentioned as cycloalkyl radicals are the cyclopropyl, cyclobutyl, cyclopentyl and cyclohexyl radicals; such radicals and also the phenyl radical can be optionally bound by way of a methylene or dimethylene group and can carry as substituents lower alkyl and/or alkoxy radicals by which are meant such radicals having 1 to 3 carbon atoms, or chlorine.

For the control of mites and ticks, thioureas more particularly suitable, by virtue or their excellent action, are those of formula I wherein $R_1$ represents Cl and $R_2$ represents $CH_3$, whilst $R_3$ and $R_4$ have the meanings given under formula I.

The thioureas of formula I can be produced by known methods, whereby in principle all conventional processes for the production of urea derivatives, including the processes usually applied for production on a commercial scale, can be used. A very advantageous process, for example, comprises the reaction of an isothiocyanate of formula II

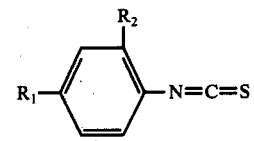

with an amine of formula III

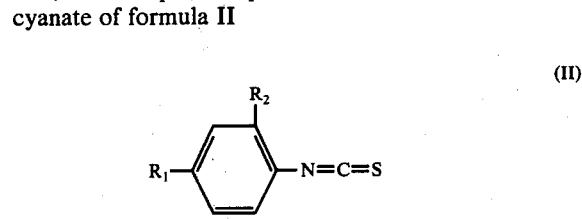

in a solvent or diluent which is inert to the reactants. $R_1$ to $R_4$ in formulae II and III have the meanings given under formula I.

The following example illustrates the aforementioned process. Temperatures are expressed in degrees centigrade.

EXAMPLE

An amount of 36.6 g of 4-chloro-2-methyl-phenylisothiocyanate is dissolved in 50 ml of benzene and this solution then added to a solution of 20 g of methylisobutylamine in 200 ml of hexane. On subsequent cooling, 52 g of 1-methyl-1-isobutyl-3-(2-methyl-4-chlorophenyl)-thiourea crystallizes out. The product has a melting point of 93°–94°.

The following thioureas of formula I are obtained in an analogous manner:

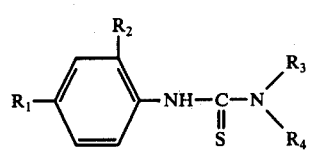

| $R_1$ | $R_2$ | $R_3$ | $R_4$ | Melting points: |
|---|---|---|---|---|
| Cl | $CH_3$ | $CH_3$ | $C_2H_5$ | 113°–114° |
| Cl | $CH_3$ | $CH_3$ | $C_3H_7$(n) | 110°–112° |
| Cl | $CH_3$ | $CH_3$ | $C_3H_7$(iso) | 134°–135° |
| Cl | $CH_3$ | $CH_3$ | $C_4H_9$(n) | 89°–90° |
| Cl | $CH_3$ | $CH_3$ | $C_4H_9$(sec) | 99°–101° |
| Cl | $CH_3$ | $CH_3$ | —CH($CH_3$)—$CH_2$—$CH_2$—$CH_3$ | 83°–85° |
| Cl | $CH_3$ | $CH_3$ | —CH($CH_3$)—CH($CH_3$)$_2$ | 147°–148.5° |
| Cl | $CH_3$ | $CH_3$ | —$CH_2$—$CH_2$—CH($CH_3$)$_2$ | 125° |
| Cl | $CH_3$ | $CH_3$ | —CH($C_2H_5$)$_2$ | 124°–125° |
| Cl | $CH_3$ | $CH_3$ | $C_5H_{11}$(n) | 88° |
| Cl | $CH_3$ | $CH_3$ | $C_4H_9$(tert) | 75° |
| Cl | $C_2H_5$ | $CH_3$ | $C_3H_7$(n) | 85°–87° |
| Cl | $CH_3$ | $CH_3$ | —$CH_2$—C($CH_3$)=$CH_2$ | 85° |
| Cl | $CH_3$ | $CH_3$ | —$CH_2CH_2OH$ | 95° |
| Cl | $CH_3$ | —$CH_2$—CH=$CH_2$ | —$C_4H_9$(iso) | 98°–99° |
| Cl | $CH_3$ | $CH_3$ | —$CH_2CH_2CN$ | 114° |
| Cl | $CH_3$ | $CH_3$ | 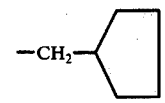 | 110° |

-continued

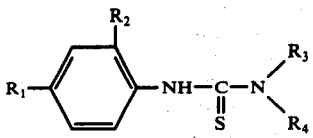
(I)

| R₁ | R₂ | R₃ | R₄ | Melting points: |
|---|---|---|---|---|
| Cl | CH₃ | CH₃ | —CH₂—C₆H₅ | 122°–123° |
| Cl | CH₃ | CH₃ | —CH₂—(tetrahydrofuryl) | 77°–79° |
| CH₃ | CH₃ | CH₃ | C₅H₁₁(n) | 78°–79° |
| CH₃ | CH₃ | CH₃ | —CH₂—CH₂—CH(CH₃)₂ | 97°–98° |
| CH₃ | CH₃ | CH₃ | —CH(CH₃)₂—CH(CH₃)₂ | 129°–130° |
| CH₃ | CH₃ | CH₃ | —CH(CH₃)—CH₂—CH₂—CH₃ | 78°–80° |
| CH₃ | CH₃ | CH₃ | —CH(C₂H₅)₂ | 106°–107° |
| CH₃ | CH₃ | CH₃ | —CH₂—CH₂—OH | 113°–115° |
| CH₃ | CH₃ | CH₃ | C₂H₅ | 136°–138° |
| CH₃ | CH₃ | CH₃ | C₃H₇(n) | 117°–118° |
| CH₃ | CH₃ | CH₃ | C₃H₇(iso) | 84°–86° |
| CH₃ | CH₃ | CH₃ | C₄H₉(n) | 80°–81° |
| CH₃ | CH₃ | CH₃ | C₄H₉(sec) | 76°–77° |
| CH₃ | CH₃ | CH₃ | C₄H₉(iso) | 75.5°–76.5° |
| CH₃ | CH₃ | CH₃ | —CH₂—C₆H₅ | 121°–122.5° |
| Br | CH₃ | CH₃ | C₄H₉(n) | 85° |
| Br | CH₃ | CH₃ | C₂H₅ | 114°–116° |
| Br | CH₃ | CH₃ | C₃H₇(iso) | 134°–136° |
| Br | CH₃ | CH₃ | C₃H₇(n) | 113°–115° |
| Br | CH₃ | CH₃ | —CH₂—(tetrahydrofuryl) | 93° |
| Br | CH₃ | CH₃ | C₄H₉(iso) | 109°–111° |
| Br | CH₃ | CH₃ | C₄H₉(sec) | 79°–81° |
| Br | CH₃ | CH₃ | —CH₂—CH₂—CN | 138°–139.5° |
| Br | CH₃ | CH₃ | —CH₂—C₆H₅ | 127°–128° |
| F | CH₃ | CH₃ | C₂H₅ | 116° |
| F | CH₃ | CH₃ | n-C₃H₇ | 101° |
| F | CH₃ | CH₃ | C₄H₉(sec) | 106° |
| F | CH₃ | CH₃ | C₄H₉(iso) | 101° |
| F | CH₃ | CH₃ | C₄H₉(n) | 82° |
| F | CH₃ | CH₃ | —CH(CH₃)(CH₂—CH₂—CH₃) | 88°–90° |
| F | CH₃ | CH₃ | —CH₂—CH₂—CH(CH₃)₂ | 87°–88° |
| F | CH₃ | CH₃ | C₄H₉(n) | 82° |
| F | CH₃ | CH₃ | —CH(CH₃)—CH(CH₃)₂ | 135°–137° |

The thioureas of formula I possess excellent properties for the control of arachnida, and of all their development stages, occurring as parasites on animals.

The said thioureas can be employed against arachnida, e.g., such as Dermanyssidae, Demodicidae, Trombiculidae, Sarcoptidae, Psoroptidae, Acaridae, Argasidae and Ixodidae.

They are particularly valuable for the control of the following ticks: *Ornithodorus moubata, Argas reflexus,* Ixodes (3-phase), *Dermacentor reticulatus* (3-phase), *Rhipicephalus spec.* (2-phase), *Rhipicephalus appendiculatus, Rhipicephalus evertsi, Boophilus microplus* (1-phase), *Boophilus decoloratus* and *Amblyomma spec.*

The action is determined by a brief immersion of adult ticks and tick larvae in aqueous emulsions of the individual active substances. The concentrations of the active substances are varied in the tests. An evaluation is made on the basis of a determination of the concentration necessary to effect a 100% destruction of the test insects.

For the widening of the range of action, it is possible to add to the active substances of formula I, in addition to acaricides and insecticides, e.g., also fungicides, bactericides, fungistatics, bacteriostatics and/or nematocides.

The compounds of formula I can be used on their own or together with suitable carriers and/or additives. Suitable carriers and additives may be solid or liquid, and correspond to the substances common in formulation practice, such as, e.g., natural and regenerated substances, solvents, dispersing agents, wetting agents, adhesives, thickeners, binders and/or fertilizers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms:

solid preparations:
  dusts,
  granulates
liquid preparations:
  a. water dispersible active substance concentrates: wettable powders, pastes, emulsions;
  b. solutions, sprays.

The solid preparations (dusts, scattering agents) are produced by the mixing of the active substances with solid carriers. Suitable carriers are, e.g. kaolin, talcum, bole, loess, chalk, limestone, ground limestone, attapulgite, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilizers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily prepared by a process in which an active substance of formula of formula I is dissolved in an organic solvent, the solution this obtained applied to a granulated mineral, e.g., attapulgite, SiO$_2$, granicalcium, bentonite, etc., and the organic solvent then evaporated off.

It is possible also to produce polymer granulates; in this case the active substances of formula I are mixed with polymerizable compounds (urea/formaldehyde; dicyandiamide/formaldehyde; melamine/formaldehyde, or others); polymerization is then carefully carried out in a manner which leaves the active substances unaffected, and granulation performed actually during the gel forming process. It is more favorable, however, to impregnate finished porous polymer granules (urea/-formaldehyde, polyacrylonitrile, polyester and others), having a specific surface area and a favourable predeterminable adsorption/desorption ratio, with the active substances, e.g., in the form of their solutions (in a low-boiling solvent), and to then remove the solvent. Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeroplanes.

Granulates can also be obtained by the compacting of the carrier material with the active substances and additives, and a subsequent reducing operation.

Moreover, it is possible to add to these mixtures additives stabilising the active substance and/or nonionic, anion-active and cation-active substances which improve, e.g., the adhesiveness of the active substances on plants and parts of plants (adhesives and agglutinants), and/or ensure a better wettability (wetting agents) as well as dispersibility (dispersing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, lignin-sulphonic acid, the alkali metal and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e., wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g., condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foam agents are, e.g., silicone oils.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylene, toluene, dimethylsulphoxide, and mineral oil fractions boiling in the range of 120° to 350° C. The solvents must be practically odorless, not toxic to plants and animals and inert to the active substances.

Furthermore, the agents according to the invention can be used in the form of solutions. For this purpose, the active substance, or several active substances, of the general formula I is (or are) dissolved in suitable organic solvents, solvent mixtures or water. As organic solvents, it is possible to use aliphatic and aromatic hydrocarbons, their chlorinated derivatives, alkylnaphthalenes, mineral oils on their own or in admixture with each other.

The content of active substance in the above described agents is between 0.1 and 95%.

The active substances of formula I can be made up, for example, in the form of the following preparations; the term 'parts' denotes parts by weight:

a.
50 parts of 1-n-butyl-1-methyl-3-(2-methyl-4-chlorophenyl)-thiourea,
5 parts of precipitated silicic acid,
3.5 parts of octylphenol polyglycol ether,
1.5 parts of N-alkyl-benzimidazolesulphonate,
0.3 part of oleic acid, and
39.7 parts of kaolin;

b.
600 g of 1-sec-butyl-1-methyl-3-(2-methyl-4-chlorophenyl)-thiourea,
50 g of sulphite liquor,
50 g of ethylene glycol, and
480 g of water.

The active substances are very finely ground with the additives in suitable grinding mils (e.g., air-jet mill or sand mill). Suspensions of any desired concentration can be prepared from the above concentrates by dilution with water. Such suspensions are particularly suitable as cattle dips.

We claim:

1. A method for combatting mites and ticks which comprises applying thereto a pesticidally effective amount of a compound of the formula

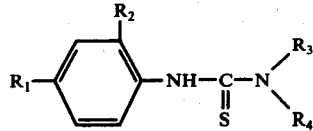

wherein $R_1$ represents halogen or methyl, $R_2$ represents $C_1$–$C_4$ alkyl, and $R_4$ represents $C_2$–$C_5$ alkyl.

2. A method according to claim 1 in which $R_1$ represents chlorine or bromine, and $R_2$ represents methyl or ethyl.

3. The method according to claim 2 in which the compound is 1-n-propyl-1-methyl-3-(2-methyl-4-chlorophenyl)-thiourea.

4. A method according to claim 2 in which $R_1$ represents chlorine and $R_2$ represents methyl.

5. The method according to claim 4 in which the compound is 1-isobutyl-1-methyl-3-(2-methyl-4-chlorophenyl)-thiourea.

6. The method according to claim 4 in which the compound is 1-ethyl-1-methyl-3-(2-methyl-4-chlorophenyl)-thiourea.

7. The method according to claim 4 in which the compound is 1-n-propyl-1-methyl-3-(2-methyl-4-chlorphenyl)-thiourea.

8. The method according to claim 4 in which the compound is 1-isopropyl-1-methyl-3-(2-methyl-4-chlorophenyl)-thiourea.

9. The method according to claim 4 in which the compound is 1-n-butyl-1-methyl-3-(2-methyl-4-chlorophenyl)-thiourea.

10. The method according to claim 4 in which the compound is 1-sec.butyl-1-methyl-3-(2-methyl-4-chlorophenyl)-thiourea.

11. The method according to claim 4 in which the compound is 1-tert.-butyl-1-methyl-3-(2-methyl-4-chlorophenyl)-thiourea.

* * * * *